United States Patent
Weber et al.

(10) Patent No.: US 6,659,941 B2
(45) Date of Patent: Dec. 9, 2003

(54) BALLOON ASSISTED ENDOSCOPE FOR VIEWING A FETUS DURING DELIVERY

(75) Inventors: Bryan Weber, Livermore, CA (US); John Walsh, Berkeley, CA (US)

(73) Assignee: Mallinckrodt, Inc., Hazelwood, MO (US)

(*) Notice: Subject to any disclaimer, the term of this patent is extended or adjusted under 35 U.S.C. 154(b) by 0 days.

(21) Appl. No.: 09/920,996

(22) Filed: Aug. 1, 2001

(65) Prior Publication Data

US 2002/0193660 A1 Dec. 19, 2002

Related U.S. Application Data

(60) Provisional application No. 60/299,368, filed on Jun. 19, 2001.

(51) Int. Cl.[7] ............................................. A61B 1/005
(52) U.S. Cl. .................. 600/116; 600/170; 600/176; 600/104
(58) Field of Search .................. 600/103, 104, 600/115, 116, 170, 118, 176, 167, 182, 338, 376, 511

(56) References Cited

U.S. PATENT DOCUMENTS

| | | | |
|---|---|---|---|
| 3,690,769 A | * 9/1972 | Mori | ............................ 356/41 |
| 4,224,929 A | * 9/1980 | Furihata | ...................... 600/116 |
| 5,099,842 A | 3/1992 | Mannheimer et al. | |
| 5,152,277 A | 10/1992 | Honda et al. | |
| 5,228,440 A | 7/1993 | Chung et al. | |
| 5,247,932 A | 9/1993 | Chung et al. | |
| 5,323,776 A | 6/1994 | Blakeley et al. | |
| 5,377,675 A | 1/1995 | Ruskewicz et al. | |
| 5,419,312 A | * 5/1995 | Arenberg et al. | ............ 600/108 |
| 5,425,362 A | 6/1995 | Siker et al. | |
| 5,497,771 A | 3/1996 | Rosenheimer | |
| 5,529,064 A | 6/1996 | Rall et al. | |
| 5,547,455 A | 8/1996 | McKenna et al. | |
| 5,551,424 A | 9/1996 | Morrison et al. | |
| 5,634,459 A | 6/1997 | Gardosi | |
| 5,681,277 A | * 10/1997 | Edwards et al. | ............... 604/22 |
| 5,839,439 A | 11/1998 | Nierlich et al. | |
| 5,916,155 A | * 6/1999 | Levinson et al. | ............ 600/338 |
| 5,987,351 A | * 11/1999 | Chance | ......................... 600/473 |
| 6,134,460 A | * 10/2000 | Chance | ......................... 600/342 |
| 6,277,066 B1 | * 8/2001 | Irwin | ........................... 600/115 |

* cited by examiner

*Primary Examiner*—John P. Leubecker
(74) *Attorney, Agent, or Firm*—Townsend and Townsend and Crew, LLP

(57) ABSTRACT

A system for visually monitoring the position of a fetal probe in relation to a fetus includes a housing having a longitudinal axis, a first side and a second side, wherein the first and second sides are on substantially opposite sides of the longitudinal axis. An optical imaging assembly is positioned on the housing to visualize along the first side, and a sensor assembly and a spacing mechanism are positioned on a first side of the housing. The spacing mechanism creates a space between the optical imaging assembly and the fetus so as to provide a wide field of view for the optical imaging assembly.

19 Claims, 4 Drawing Sheets

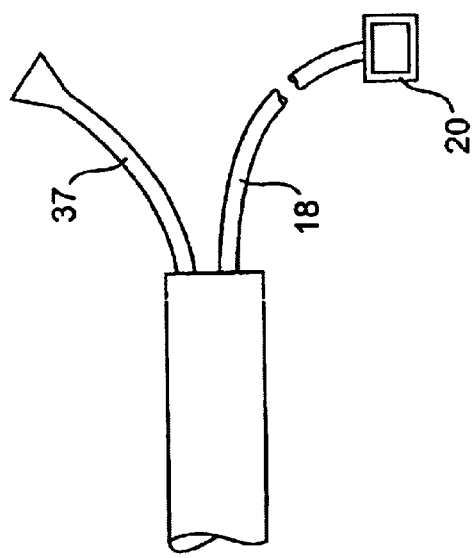
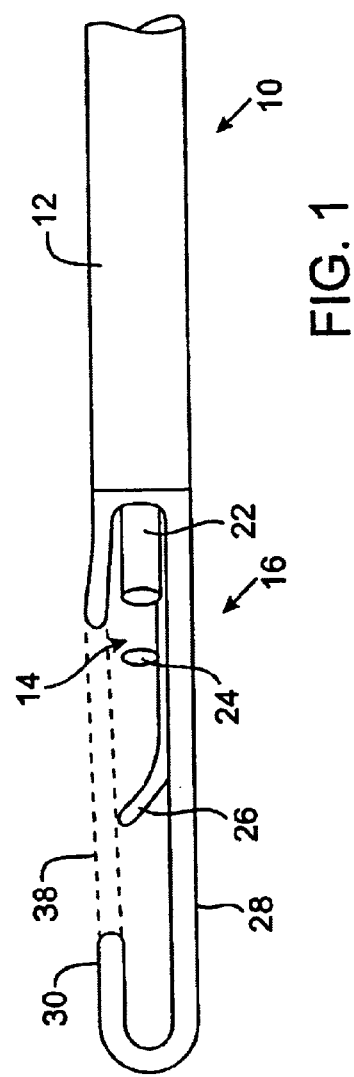
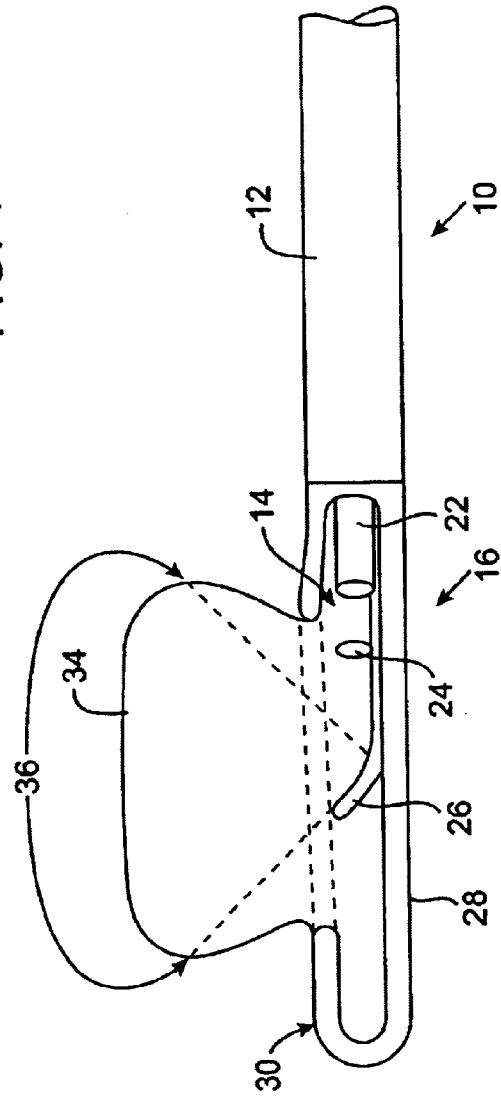
FIG. 1
FIG. 2

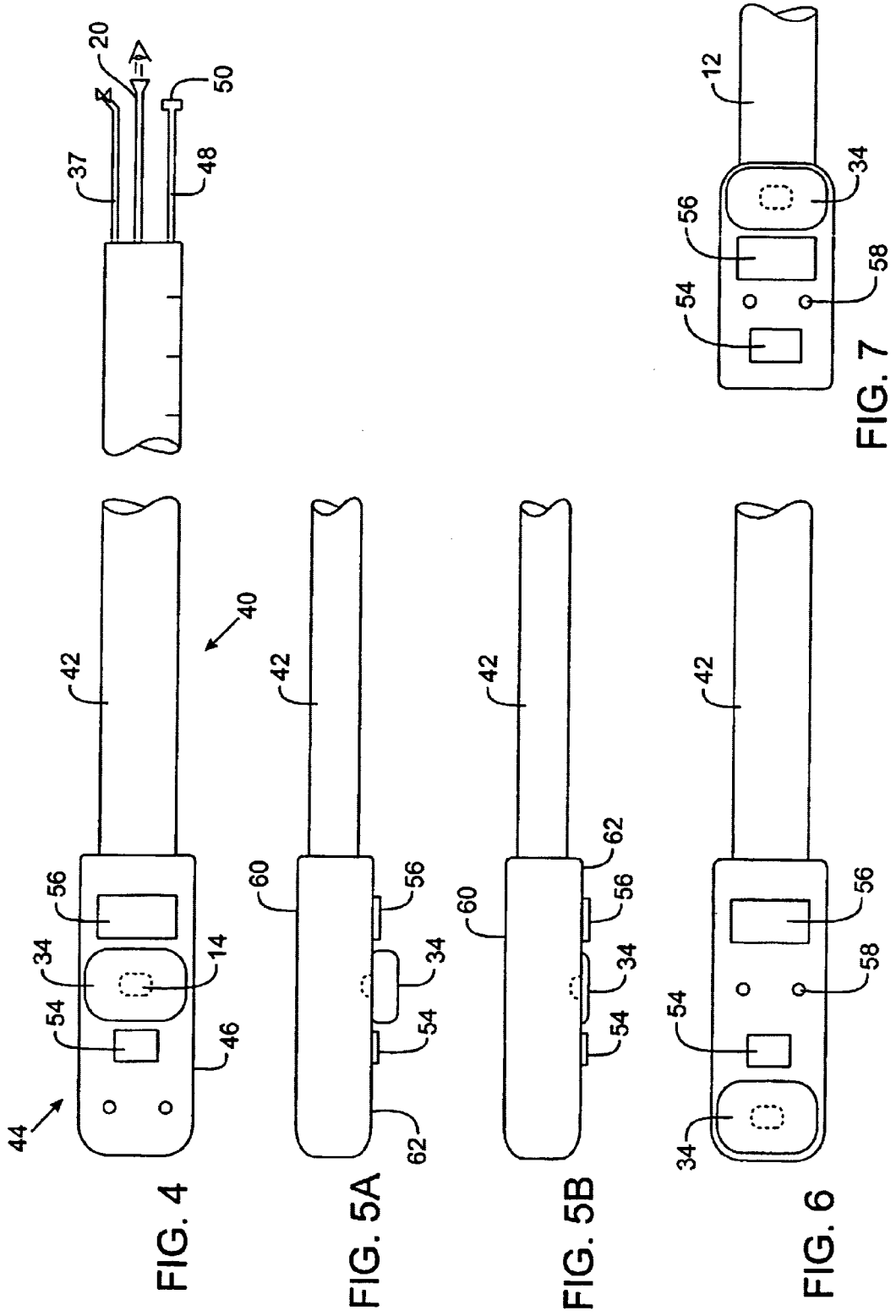

BALLOON ASSISTED ENDOSCOPE FOR VIEWING A FETUS DURING DELIVERY

CROSS-REFERENCES TO RELATED APPLICATIONS

The present application claims benefit of Provisional Patent Application Serial No. 60/229,368, filed Jun. 19, 2001, and entitled "A Fetal Probe Having an Optical Imaging Device," and is related to U.S. patent application Ser. No. 09/921,287, filed concurrently herewith, entitled "A Fetal Probe Having an Optical Imaging Device," the complete disclosures of which are incorporated herein by reference for all purposes.

BACKGROUND OF THE INVENTION

The present invention relates generally to probes for monitoring the condition of a fetus and/or the in utero environment, and more specifically to fetal probes having improved visual monitoring.

During in utero labor and delivery of a fetus, fetal probes are used to monitor the health of the fetus. Fetal probes having pulse oximeters are typically used to measure various blood characteristics including arterial blood oxygen saturation and pulse rate. Pulse oximetry sensors pass light through a portion of the fetus' skin and photo-electrically detect pulsatile changes in the absorption of the light by the tissue. The detected light is then used to determine the characteristic of interest.

In order to achieve accurate measurements, the aforementioned sensing devices must maintain contact with the fetus at an appropriate part of the fetus' body. The quality of the optical signal generated by the pulse oximeter sensor depends, in part, on the placement of the sensors on the fetus' body and on the quality of optical coupling between the sensor and the patient. The quality of optical coupling is related to the amount of light emitted by the sensor that actually enters the fetus' tissue and to the portion of the light received by the sensor that actually passes through the fetus' blood-perfused tissue.

Tissue characteristics at the sensor site can affect the quality of the optical coupling between the sensor and the patient. The presence of hair or vernix on the skin will attenuate the light transmitted into the tissue by the sensor. For example, if the sensor is placed over dense hair, the system may not be able to appropriately process the signal. Consequently, it is important that the physician position and orient the fetal probe at a proper place on the fetus.

One method of placing the fetal probe adjacent the fetus is through manual assessment of the womb to determine the orientation of the head of the fetus and depth of the fetus within the womb. Once the physician has determined the position of the fetus, the physician picks a line of entry and introduces the fetal probe along the line to try to place the fetal sensors on the fetus' cheek. Unfortunately, the physician will only have tactile feedback in regards to the positioning of the sensors and will have no visual indication of the position of the fetal sensors relative to the fetus. If the physician has misassessed the position of the fetus and has not placed the fetal probe adjacent the fetus' cheek, the physician will have a difficult time in correctly positioning the fetal probe.

Accordingly, what is needed are systems and methods that allow the user to monitor the location at which the fetal sensor was, is, or will be placed within the womb.

SUMMARY OF THE INVENTION

The present invention generally provides improved systems and methods for improved visual monitoring of a fetus in utero. In particular, the present invention provides improved methods and systems of improved visual monitoring of the placement of fetal sensors in utero. The probes of the present invention generally include an optical imaging assembly, and a spacing mechanism that creates a space between the imaging assembly and the fetus so as to provide a wide field of view for the imaging assembly.

The fetal probes of the present invention will generally include an imaging device, such as an optical fiber bundle, an optical conduit, CCD camera, or the like. The imaging device can be coupled to a distal housing of the fetal probe to visually image and/or illuminate the same or nearby region of the in utero environment or fetus that is adjacent the distal housing. The images from the illuminated portion of tissue are transmitted through the imaging device to an optical viewing device such as a hand-held image viewing instrument, camera, or a video monitor.

In some exemplary embodiments, the fetal probe will include fetal oximetry sensors that have a light emitter (e.g., an LED) and a light detecting sensor. The light emitter can emit an infrared light, a visible light, or the like. The imaging device can be positioned adjacent the fetal oximetry sensors so as to provide a visual indication of the position of the fetal sensors relative to the fetus' tissue.

In some arrangements, the light emitter can be used for multiple purposes, such as for both spectral pulse oximetry and for illuminating the fetus' tissue for visual examination. Alternatively, a separate illumination source (e.g., such as an optical fiber coupled to a broad spectrum light source) can be used to provide illumination for the visualization of the region of the fetus.

The light detecting sensors can be configured to sense the light emitted from the light emitter for pulse oximetry purposes. However, in some arrangements, the light detecting sensors can also be configured to detect the light for visualization purposes. For example, a light sensor can vary its mode of operation to be able to both detect pulse oximetry data and to provide visual images of the fetus. In such embodiments, the pulse oximetry light detecting sensor will have a dual function and the separate imaging device will not be needed.

The spacing mechanisms of the present invention can take a variety of forms. In an exemplary embodiment, the spacing mechanism is an inflatable bladder or balloon that can be positioned between the fetus and distal housing. In one configuration, the inflatable bladder can be filled with a clear medium, such as saline, to provide space between the imaging assembly and the fetus. Because the inflatable bladder and the clear medium are positioned between the fetus and the imaging assembly, bodily fluids such as blood, amniotic fluid, vernix, and mucus are displaced from the field of view of the imaging assembly and do not substantially interfere with the imaging optics. The imaging device allows the physician to continuously monitor the sensor placement site during initial placement of the sensor. As an additional benefit, the imaging device can be used to monitor the position and orientation of the fetus during labor and delivery.

In one aspect, the present invention provides a probe for viewing a fetus. The probe comprises an imaging assembly positioned on a body. A spacing mechanism is disposed on the body to create a space between the imaging assembly and the fetus and/or the in utero environment. The spacing mechanism provides the space to provide a larger field of view for the imaging assembly. In some methods of use, the spacing mechanism will contact the fetus or the in utero environment. In other methods of use, the spacing mechanism will only displace body fluids, such as amniotic fluids, but will not contact the fetus.

In another aspect, the present invention provides a fetal probe system for monitoring a fetus. The system includes a fetal sensor assembly disposed on the body. An optical imaging assembly is positioned adjacent the fetal sensor assembly to visualize the portion of the fetus adjacent the fetal sensor assembly. An expandable spacing mechanism is positioned between the optical imaging assembly and the fetus to create a space between the optics assembly and the fetus.

In a further aspect, the present invention provides a method of monitoring a fetus. The method comprises placing a probe adjacent the fetus. A space is created between the fetus and the probe, and the fetus is imaged with an imaging assembly. An image of a portion of the fetus and/or the in utero environment is transmitted to a viewing display so as to provide a visual indication of the position of the fetus in relation to the fetal probe.

In yet another aspect, the present invention provides a method of displacing body fluids to allow clearer imaging of a target tissue. The method comprises placing a probe adjacent the target tissue. A displacement mechanism is positioned between the target tissue and the probe to displace body fluids (e.g., amniotic fluids, meconium tissue, and the like) so as to provide a field of view for imaging the target tissue. In exemplary methods, the method can be used to image a fetus or in utero environment. It should be appreciated however, that the displacement mechanism can also be used in other non-invasive, minimally invasive, or open surgical procedures.

For a further understanding of the nature and advantages of the invention, reference should be made to the following description taken in conjunction with the accompanying drawings.

BRIEF DESCRIPTION OF THE DRAWINGS

FIG. 1 is a plan view of a fetal probe of the present invention with a spacing mechanism in an unexpanded position;

FIG. 2 is a partial plan view of the fetal probe of FIG. 1 with the spacing mechanism in an expanded position;

FIG. 4 is a plan view of a fetal probe having a spacing mechanism positioned between a sensor assembly;

FIG. 5A is a partial cross sectional side view of the fetal probe of FIG. 4 with the spacing mechanism in an expanded position;

FIG. 5B is a partial cross sectional side view of the fetal probe of FIG. 4 with the spacing mechanism in a unexpanded position;

FIG. 6 shows an alternative fetal probe having a spacing mechanism positioned distal of the sensor assembly;

FIG. 7 shows an alternative fetal probe having a spacing mechanism positioned proximal of the sensor assembly;

DESCRIPTION OF THE SPECIFIC EMBODIMENTS

Figure 3:
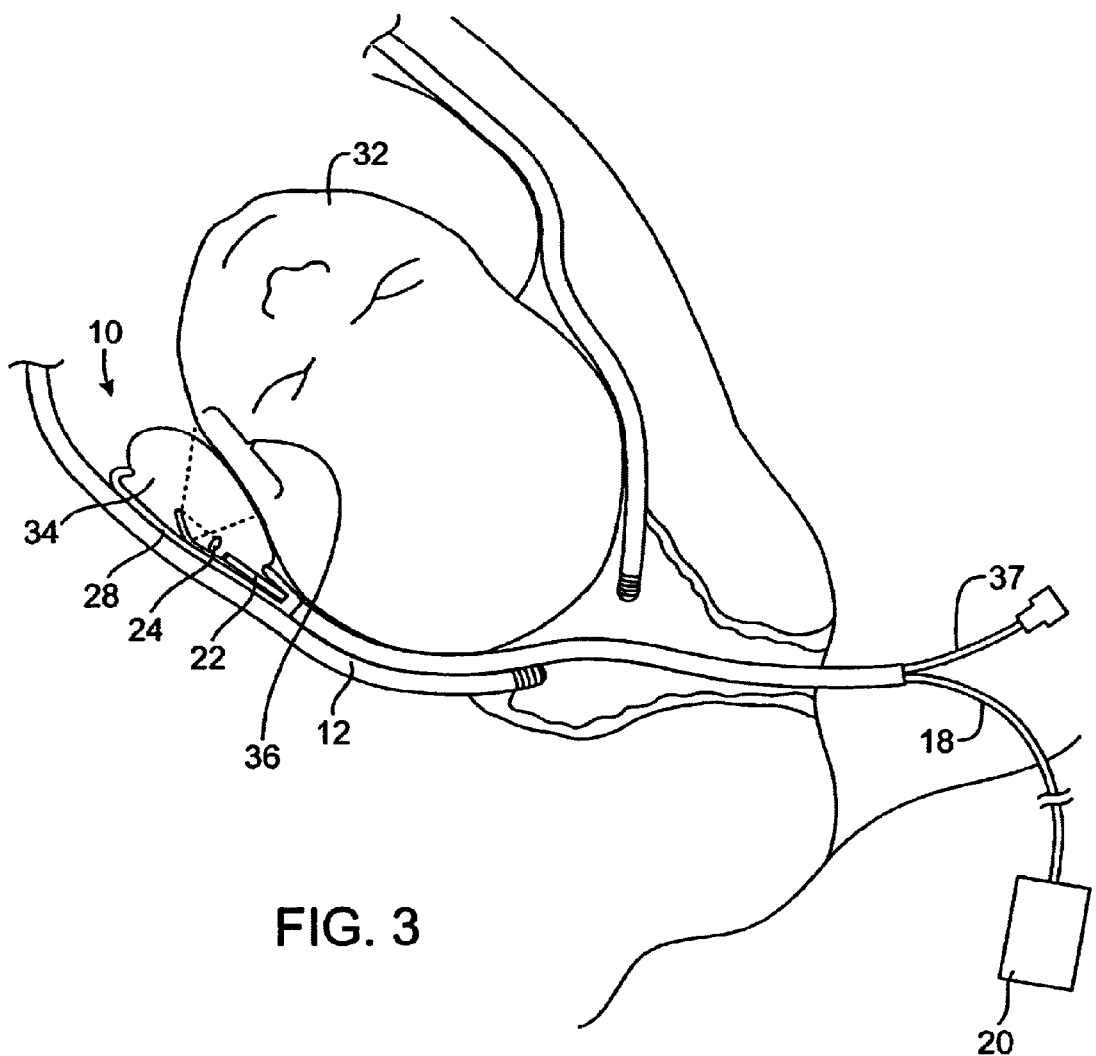
FIG. 3 illustrates the fetal probe of FIG. 1 positioned adjacent a fetus head.
Figure 8:
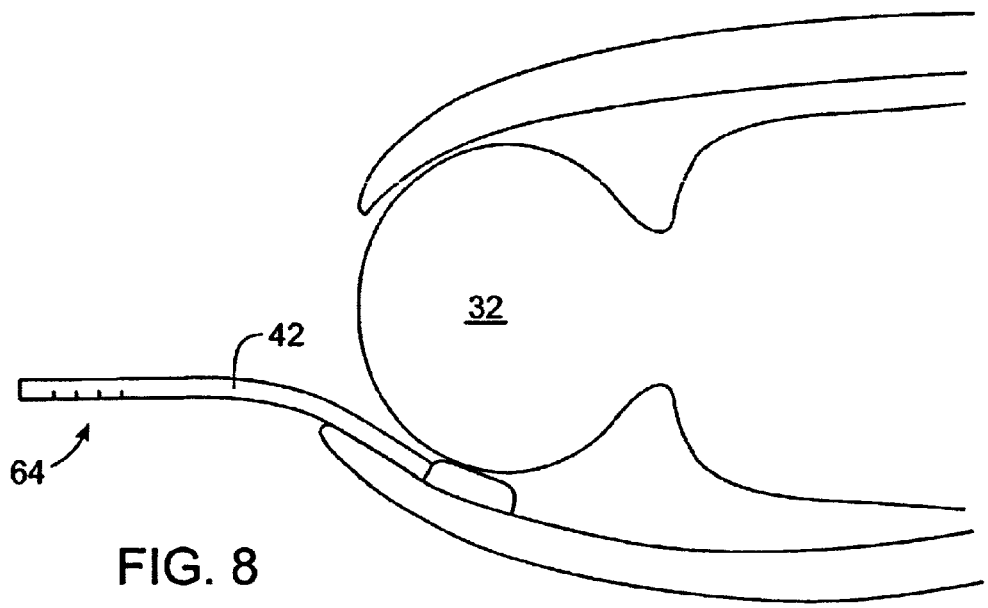
FIG. 8 illustrates an initial placement of the fetal probe in the womb with the spacing mechanism in an unexpanded position.
Figure 9:
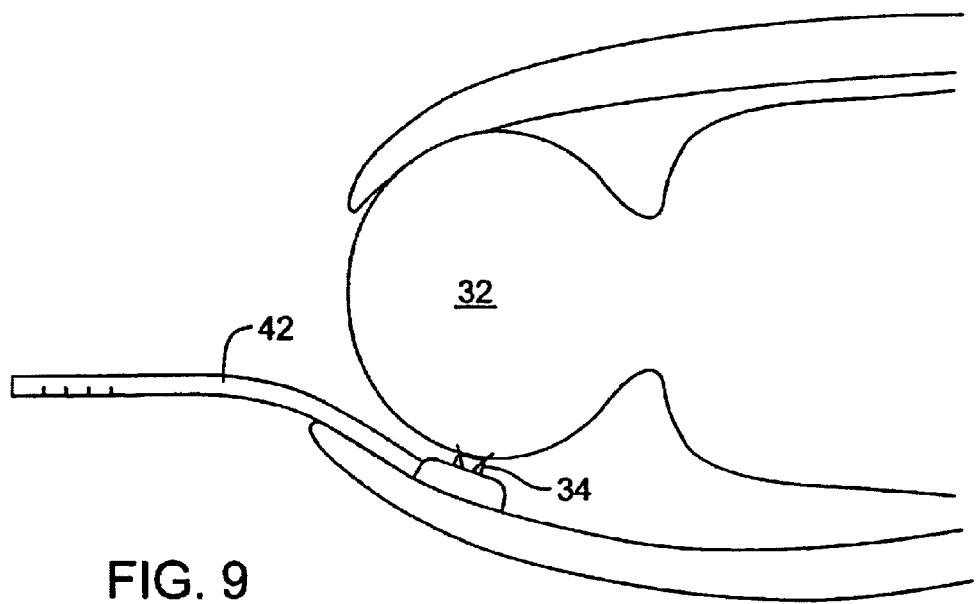
FIG. 9 illustrates the fetal probe with the spacing mechanism in an expanded position so as to provide a field a view for the imaging device.

FIG. 1 illustrates a probe 10 incorporating the concepts of the present invention. The probe 10 includes an elongate housing 12 which is coupled to a distal body 16. An imaging assembly 14 are positioned on the distal body 16. A cable 18 connects the imaging assembly 14 to a viewing device 20. In an exemplary embodiment, the imaging assembly 14 includes a fiber bundle 22, a lens 24, and a mirror 26. An image of a region of the fetus can be reflected off the mirror 26 through the lens 24 and delivered to the optical fiber bundle 22. Other embodiments of the probe may include a separate light source (not shown) to illuminate the target area. The distal end portion of the probe 10 has a maternal or non-active surface 28, and an active or fetal surface 30 which is adapted to be placed against a portion of a target tissue (e.g., the fetus 32; FIGS. 3, 8, and 9). A spacing mechanism 34 is disposed at the distal portion of the probe 10 so as to space the active surface 30 and imaging assembly 14 from the fetus. As illustrated in FIGS. 1 and 2 in exemplary embodiments, the spacing mechanism 34 can be moved from an unexpanded configuration (FIG. 1) to an expanded configuration (FIG. 2) to provide a wide field of view 36 for imaging device.

While not shown, it should be appreciated that the concepts of the present invention are applicable to other imaging or fetal probes. For example, the fetal probes may include, fetal oximetry sensors, an IUP transducer, an ECG electrode, a temperature probe, or the like disposed on the distal portion of the fetal probe.

In most embodiments the spacing mechanism 34 is movable from the unexpanded position to the expanded configuration through introduction of a medium, (such as a fluid or a gas) into the spacing mechanism 34. In most embodiments, the spacing mechanism is a substantially clear, expandable bladder that is positioned on the fetal surface 30 between the imaging assembly 14 and the fetus 32. An inflation channel 37 extends from the expandable bladder 34 through the shaft to a fluid or gas supply (not shown). Using conventional means, a clear liquid or gas is delivered to the bladder 34 so that the bladder expands (FIG. 2). The spacing mechanism displaces any bodily fluids that are between the optical imaging assembly and the fetus, and creates space between the fetus 32 and the imaging assembly 14 so that the imaging assembly 14 can image a portion of the fetus with a reasonable field of view.

In most configurations, the expanded bladder 34 at least partially covers the active surface 30 of the elongate housing 12 to provide spacing between the optical imaging assembly 14 and the fetus 32. In the unexpanded configuration the bladder 34 is typically stored within an opening 38 in the distal end of the elongate housing 12. Once the gas or liquid is delivered to the bladder 34, the bladder can expand through the opening 38 towards the fetus 32 to create spacing for the optical assembly 14. Bladder 34 is typically made of a folded or elastic material, such as a thin plastic bellows, polyurethane films, synthetic membranes, synthetic rubber material, or other materials that allow inflation and deflation.

In use, the probe 10 is inserted into the cervix in a flattened or unexpanded configuration. Once the probe 10 has been positioned adjacent the fetus 32, a fluid or gas can be delivered from a source (not shown) through the inflation channel 36 to inflate the bladder 34. The expanded bladder 34 can then move the non-active surface 28 of the elongate housing 12 against the maternal tissue M and can move the active face 30 (and optical imaging assembly 14) away from the fetus 32. As shown in FIG. 3, the expanded bladder 34 can contact a portion of the fetus so that amniotic fluid, blood, mucus, meconium, and the like is displaced and does not interfere with the field of view of the imaging assembly 14. In other embodiments, expanded bladder 34 can merely displace the body fluids without contacting the fetus.

Furthermore, the bladder 34 creates a spacing between the optics assembly 14 and the fetus 32 that provides a wide field of view that allows the physician to monitor the position of the fetus and determine if the probe 10 is in a proper position adjacent the fetus 32. It may be possible to adjust the focus of the imaging assembly by increasing or decreasing the size of the bladder by increasing or decreasing the amount of air or liquid that is delivered into the bladder.

Delivery of the probe 10 through the cervix to the fetus can occur prior to sensor placement as a tool for confirming fetal position and for identifying the subsequent sensor placement site. For example, in one method of the present invention, the probe 10 is inserted into the cervix to a target position where the physician plans on positioning the fetal probe. If it is visually determined that the target position is proper (e.g., that the target site does not contain hair or mucus), the bladder can be deflated and the probe 10 can be removed. Thereafter, the sensors can be delivered into the cervix and to the target position. Alternatively, the probe 10 having the expandable bladder can be delivered to the target site after sensor placement to confirm proper sensor placement.

It should be appreciated that the present invention provides a variety of configurations of the probe 10. For example, FIG. 4 illustrates a fetal probe 40 incorporating the concepts of the present invention. The fetal probe 40 includes a shaft 42 which has a fetal sensor assembly 44 positioned at a distal end portion 46 of the shaft. A cable 48 connects the fetal sensor assembly 44 to a connector 50 that is disposed near a proximal end 52 of the shaft. Fetal sensor assembly 44 typically includes a light source 54 and a light detector 56. In some embodiments, the fetal sensor assembly 44 can also include other sensors or electrodes 58. The distal end portion of the shaft 46 has an inactive or maternal surface 60 and an active or fetal surface 62 which is adapted to be placed against a fetus 32 (FIGS. 5A and 5B). An optical imaging assembly 14 is disposed on the distal end portion 56 of the shaft to provide visual feedback to the physician and to aid in placement of the fetal sensor assembly 44. As shown above, some embodiments of the optical imaging assembly 14 can include a lens and mirror (not shown). A spacing mechanism 34 is positioned between the optical imaging assembly 14 so as to space the active surface 62 and imaging assembly 14 from the fetus 32. A more complete description of fetal oximetry probes having visualization assemblies is described in co-pending, and commonly owned U.S. patent application Ser. No. 09/921.287, filed concurrently herewith and entitled "A Fetal Probe Having An Optical Imaging Device," the complete description of which is incorporated herein by reference.

As shown in FIGS. 5A to 7, the imaging device 34 can be positioned proximal (FIG. 6), distal (FIG. 7), or between the light source 54 and the light detector 56 (FIGS. 5A and 5B) so that the physician can view the tissue that is in the direct vicinity of the sensor assembly 14.

If it is determined that the fetal probe is not in a proper position (e.g., over hair, mucous or vernix) the physician can reposition the fetal probe. In repositioning the fetal probe, the physician can drain the bladder, or can merely reposition the bladder in its expanded state. Once the physician determines that the position of the fetal probe is sufficient to properly image the fetus, the physician can deflate the bladder 34 by removing the liquid or gas from within the bladder 34.

In one method of the present invention, the fetal probe 40 is inserted into the cervix in an unexpanded position (FIG. 8). Some embodiments of the fetal probe 40 will have external marks 64 along a proximal portion of the shaft to provide an indication of the depth of insertion of the fetal probe 40 into the cervix. Once the physician feels that the fetal probe is at the target site, the spacing mechanism can be expanded to create an adjustable field of view for an optical imaging assembly. If it is visually determined that the fetal probe 40 is positioned properly on the fetus 32, the spacing mechanism is deflated and the fetal sensor assembly is allowed to contact and monitor the fetus. If however, it is determined that the fetal probe is not properly positioned on the fetus 32, the fetal probe can be moved until it is visually determined that the fetal probe is positioned on the fetus.

As will be understood by those of skill in the art, the present invention may be embodied in other specific forms without departing from the essential characteristics thereof. For example, while not shown, it should be appreciated that the probes of the present invention can also be used to image the in utero environment, such as the uterus, placenta, umbilical cord, vernix, and the like. Furthermore, the concepts of the present invention can be used in other imaging devices for use in the patient's body.

While not shown, a biasing mechanism can also be positioned on the fetal probe housing to bias the fetal sensors against the fetus after visualization of the position of the fetal sensors has determined to be sufficient for oximetry purposes. The biasing mechanism can be used to push the fetal sensors against the fetus to improve detection of fetal blood characteristics or other desired parameters. Accordingly, the foregoing description is intended to be illustrative, but not limiting, of the scope of the invention which is set forth in the following claims.

What is claimed is:

1. A fetal probe comprising:
    a housing comprising a longitudinal axis, a fetal side, and a maternal side, wherein the fetal side and maternal side are positioned on substantially opposite sides of the longitudinal axis;
    an imaging assembly positioned on the housing to visualize along the fetal side of the housing;
    a sensor assembly coupled to the housing and positioned to monitor along the fetal side of the housing; and
    a spacing mechanism positioned on the fetal side of the housing to create a space between the imaging assembly and at least one of a fetus and an in utero environment.

2. The probe of claim 1 wherein the spacing mechanism is an expandable bladder.

3. The probe of claim 2, wherein the sensor assembly comprises an active face including a light source and a light detector, wherein upon deflation of the expandable bladder the active face can contact the fetus.

4. The probe of claim 2 wherein the expandable bladder comprises an inflation channel which can direct at least one of a fluid and a gas to the bladder.

5. The probe of claim 2, wherein the bladder pushes an inactive surface the maternal side of the housing against a maternal tissue.

6. The probe of claim 1 wherein the spacing mechanism is substantially clear.

7. The probe of claim 6 wherein the imaging assembly images the fetus through the substantially clear spacing mechanism.

8. The probe of claim 1 further comprising a handle for placing the housing at a site on the fetus beyond a transcervical region.

9. The probe of claim 1 wherein the imaging assembly is an optical fiber bundle.

10. A fetal probe system comprising:
a body comprising a longitudinal axis, a first side and a second side that are positioned on substantially opposite sides of the longitudinal axis;
a fetal sensor assembly coupled to the first side of the body and positioned to monitor at least one of a fetus and an in utero environment;
an imaging assembly coupled to the first side of the body configured to provide visualization of at least one of the fetus and the in utero environment; and
a spacing means coupled to the first side of the body and positioned to create a space between the imaging assembly and at least one of the fetus and the in utero environment.

11. The system of claim 10 wherein the spacing means creates a field of view for the imaging assembly.

12. The system of claim 10 wherein the body is pushed away from the fetus and against an uterine wall when the spacing means is expanded.

13. The system of claim 10 further comprising an illumination source coupled to the body, wherein the illumination source illuminates at least a portion of the fetus.

14. The system of claim 10 wherein the imaging assembly is operatively coupled to a display device for displaying an image of the fetus.

15. A fetal probe comprising:
a housing comprising a longitudinal axis, a first side and a second side that are positioned on substantially opposite sides of the longitudinal axis;
an imaging assembly coupled to the first side of the housing for visualizing at least one of a fetus and an in utero environment that is positioned on along the first side of the housing;
a sensor assembly coupled to the first side of the housing and positioned to monitor at least one of the fetus and the in utero environment that is positioned along the first side of the housing; and
a spacing mechanism positioned on the first side of the housing to create a space between the imaging assembly and at least one of the fetus and the in utero environment.

16. A fetal probe comprising:
a housing;
an imaging assembly coupled to the housing for visualizing at least one of the fetus and the in utero environment;
a spacing mechanism positioned on the housing to create a space between the imaging assembly and at least one of the fetus and the in utero environment, wherein the spacing mechanism is an expandable bladder; and
a sensor assembly disposed on the housing, wherein the sensor assembly comprises an active face including a light source and a light detector, wherein upon deflation of the expandable bladder, the active face can contact the fetus.

17. The probe of claim 16 wherein the expandable bladder comprises an inflation channel which can direct at least one of a fluid and a gas to the bladder.

18. The probe of claim 16 wherein the housing comprises a fetal side and a maternal side, wherein the bladder pushes the maternal side of the housing against a maternal tissue.

19. The probe of claim 16 wherein the spacing mechanism is substantially clear.

* * * * *